United States Patent

Takahashi

Patent Number: 5,257,981
Date of Patent: Nov. 2, 1993

[54] OSTOMY APPLIANCE

[75] Inventor: Tetsuya Takahashi, Kawasaki, Japan

[73] Assignee: Alcare Co. Ltd., Tokyo, Japan

[21] Appl. No.: 708,477

[22] Filed: May 31, 1991

[30] Foreign Application Priority Data

Jun. 4, 1990 [JP] Japan .................. 2-59606[U]

[51] Int. Cl.$^5$ .................................. A61F 5/44
[52] U.S. Cl. ......................... 604/342; 604/338; 604/332
[58] Field of Search ............ 604/332, 338, 342–344, 604/333–337, 339, 340, 345

[56] References Cited

U.S. PATENT DOCUMENTS

| 4,419,100 | 12/1983 | Alexander | 604/341 |
| 4,664,661 | 5/1987 | Ferguson | 604/342 |
| 4,872,869 | 10/1989 | Johns | 604/342 |
| 4,973,323 | 11/1990 | Kaczmarek et al. | 604/338 |

FOREIGN PATENT DOCUMENTS

| 0098718 | 1/1984 | European Pat. Off. | 604/332 |
| 0235563 | 9/1987 | European Pat. Off. | 604/332 |
| 0251502 | 1/1988 | European Pat. Off. | 604/332 |
| 2179556 | 3/1987 | United Kingdom | 604/332 |
| 2193097 | 2/1988 | United Kingdom | 604/332 |
| 2193893 | 2/1988 | United Kingdom | 604/332 |
| 2198953 | 6/1988 | United Kingdom | 604/332 |

Primary Examiner—Randall L. Green
Assistant Examiner—R. Clarke
Attorney, Agent, or Firm—Haverstock, Garrett & Roberts

[57] ABSTRACT

An ostomy appliance for attachment around an aperture of the human body including a plate-like member having an opening extending therethrough and being adhesively attached around such body aperture, a first flange member having an annular coupling portion and being attachable over a portion thereof to the non-adhesive side of the plate-like member adjacent the opening extending therethrough, a second flange member having an annular coupling portion associated with one side thereof and a bag-like member associated with the opposite side thereof for collecting waste products therein, the coupling portion of the second flange member being cooperatively engageable with the coupling portion of the first flange member, and a sealing member located adjacent the inner most portion of one of the coupling flange portions on the side thereof facing the opening in the plate-like member, the sealing member exerting a biasing force against the opposed coupling portion when such coupling portions are engaged with each other so as to form a pressure tight annular seal therebetween at such point of joinder to prevent any leakage between such members. Attachment of the first flange member to the plate-like member is such that a space is formed therebetween over a portion of their respective lengths to facilitate manipulating and maneuverability of such first and second flange members during operation thereof.

13 Claims, 5 Drawing Sheets

OSTOMY APPLIANCE

Applicant hereby claims foreign priority benefits under 35 U.S.C. §119 of corresponding Japanese patent application No. (Hei) 2-59606 filed Jun. 4, 1990.

INDUSTRIAL FIELD OF UTILIZATION

The present invention relates to an ostomy appliance which is easily securable to an aperture or opening formed on the surface of a human body, the appliance being used for either removing waste products from the inside of the human body or for introducing a liquid preparation into the human body.

BACKGROUND OF THE INVENTION

So-called ostomy appliances are generally furnished for receiving various waste products and waste liquids discharged from the human body and such appliances are sometimes used for introducing a liquid preparation into the human body for therapy or washing at an aperture or opening formed on or through the surface of the human body such as the fistula formed on the surface of the body by performing surgical operations such as a colostomy, ileostomy, ureterostomy and the like wherein such devices are used to combat rectal or bladder disease. Other applications include use in connection with a leading enteric canal, a ureter tube or other tube connected to the body surface or opening formed on the surface of the human body by a wound. Artificial anal appliances and artificial urinary bladder appliances are typical examples. Since ostomy appliances are to treat waste products discharged from the human body, it is necessary to perform such removal sanitarily without contacting such waste products with the skin or opening while at the same time maintaining the sanitary reliability of the device such that such waste products do not leak out during use. It is also important that such appliances be easy to put on and to take off and that they are comfortable to the skin since such devices are secured directly to the skin surface.

Various ostomy appliances have heretofore been devised and broadly employed for use in attempting to satisfy the above-described objects and requirements including so-called two piece type ostomy appliances. Typical of such so-called two piece type ostomy appliances are those constructions which include a first member having an opening or aperture extending therethrough and having a fitting element associated with one side thereof and adhesive means associated with the opposite side thereof, and a second member equipped on one side thereof with a fitting element which closely couples with that of the first member and includes a pouch or cap associated with the opposite side thereof. In these known appliances, the first member is always fixed or secured around the aperture, and the second member is coupled with the first member such that waste products are collected in the pouch associated with the second member. When the waste products are accumulated in the pouch, the second member is taken off, the waste products accumulated therein are removed therefrom, and such member can then be either washed for re-use, or it can be replaced by a totally new second member. The pouch in the second member can also be replaced by a cap type member, depending upon its use.

These known devices have several shortcomings which limit their desirableness and usefulness as effective, sanitary, comfortable and easy to use appliances. For example, in the known type of ostomy appliance described above, the effective diameter of the opening formed to correspond with the opening or aperture in the human body over which it is positioned is too small and as such effective diameter is made larger, the whole appliance becomes bigger and bulkier. Also, in such known appliances, waste products tend to pool at the inside corners of both members. This presents a sanitary problem as waste products are not properly and sanitarily captured within the pouch of the second member thereby causing possible skin irritation, odor, stains on one's clothing, and other disease related problems. Also, the known appliances cause discomfort to the patient when they are installed due to their bulkiness as a whole, and due to the fact that they are not easy to put on or take off of a patient. Furthermore, since the putting on and taking off of such known two-piece type appliances is not necessarily easy, oppressive forces in manipulating the known two-piece devices to accomplish attachment and detachment of the respective members cause pain and discomfort to the patient since such members are directly attached to the patient's skin. For these and other reasons, the known prior art ostomy devices are not entirely satisfactory.

SUMMARY OF THE INVENTION

The present ostomy device overcomes many of the above discussed disadvantages and shortcomings associated with the known prior art devices and teaches the construction and operation of a two-piece ostomy appliance which is easy and comfortable to put on and take off of a patient; it is highly reliable during use; and its operation is both easy and sanitary.

The present device can be attained by an ostomy appliance having an adhesive plate member (skin-contacting plate member) fixed by adhesion around the aperture of a human body to which it will be attached, the adhesive plate member having an opening extending therethrough corresponding to the aperture of a human body over which it will be positioned and further having a first flange member fixed to the non-adhesive side thereof. The present device also includes a second flange member capable of fitting or cooperatively engaging the first flange member and having a pouch or cap associated with the opposite side thereof. The first flange member associated with the adhesive plate member has a thin ring-form or annular sealing portion extending outwardly therefrom nearly along the surface of said adhesive plate of which the inner periphery is secured to the periphery of the opening extending through the adhesive plate member. The first flange member further includes a ring-form or annular fitting portion extending outside the annular sealing portion and extending from the surface of said adhesive plate member beyond a distance nearly in parallel with the surface of said adhesive plate, a ring-form or annular taper member connecting between the annular sealing portion and the annular fitting portion, and a prominence or groove for fitting or engaging the cooperatively engagable means associated with the second flange member. In this regard, the second flange member includes a correspondingly shaped ring-form or annular fitting portion dimensioned to fit or cooperatively engage the first flange member on one side thereof and a pouch or cap on the opposite side thereof, the annular fitting portion having a groove or prominence which cooperatively engages the prominence or groove associated with the fitting portion of the first flange member. The second flange member is further equipped with a sealing chip which exerts a resiliant type of force on the fitting portion of the first and second flange members adjacent the inner most side of said flange members facing the opening extending through the adhesive plate member, the sealing chip forming an annular seal between the first and second flange members and adjacent the opening extending through the adhesive plate member so as to prevent any leakage between such members. In the ostomy appliance of the present device the first flange member approaches the surface of the adhesive plate member and extends nearly in parallel thereto by adhering the inside circumference of the thin annular sealing portion of the first flange member directly around the opening of the adhesive plate member and forming the annular fitting member as a whole via the outwardly extending annular taper member. This means that a gap is formed by and between the fitting member and the adhesive plate over at least a portion of the length of the first flange member thereby enabling one to support the first flange member from below by inserting a finger between the adhesive plate member and the fitting member during attachment, operation, and detachment of the second flange member to the first flange member due to the flexibility of such members and the sealing portion of the first flange member. This makes for easy manipulation and maneuverability of the respective portions of the present appliance during operation thereof and it facilitates the easy removal of waste products therefrom. Furthermore, the prominence or groove associated with the fitting member of the first flange member is devised so as to fit or cooperatively engage the groove or prominence associated with the fitting member of the second flange member. When cooperatively engaged, both flange members are tightly coupled to each other and the sealing chip associated with the second flange member is firmly seated against the opposed face of the first flange member adjacent the opening extending through the adhesive plate member thereby preventing any leakage of the waste products from the human body therebetween.

These and other objects and advantages of the present invention will become apparent to those skilled in the art after considering the following detailed specification in conjunction with the accompanying drawings.

DETAILED DESCRIPTION OF THE INVENTION

Practical embodiments of the present device will now be explained hereinbelow with respect to the drawings.

Figure 1:
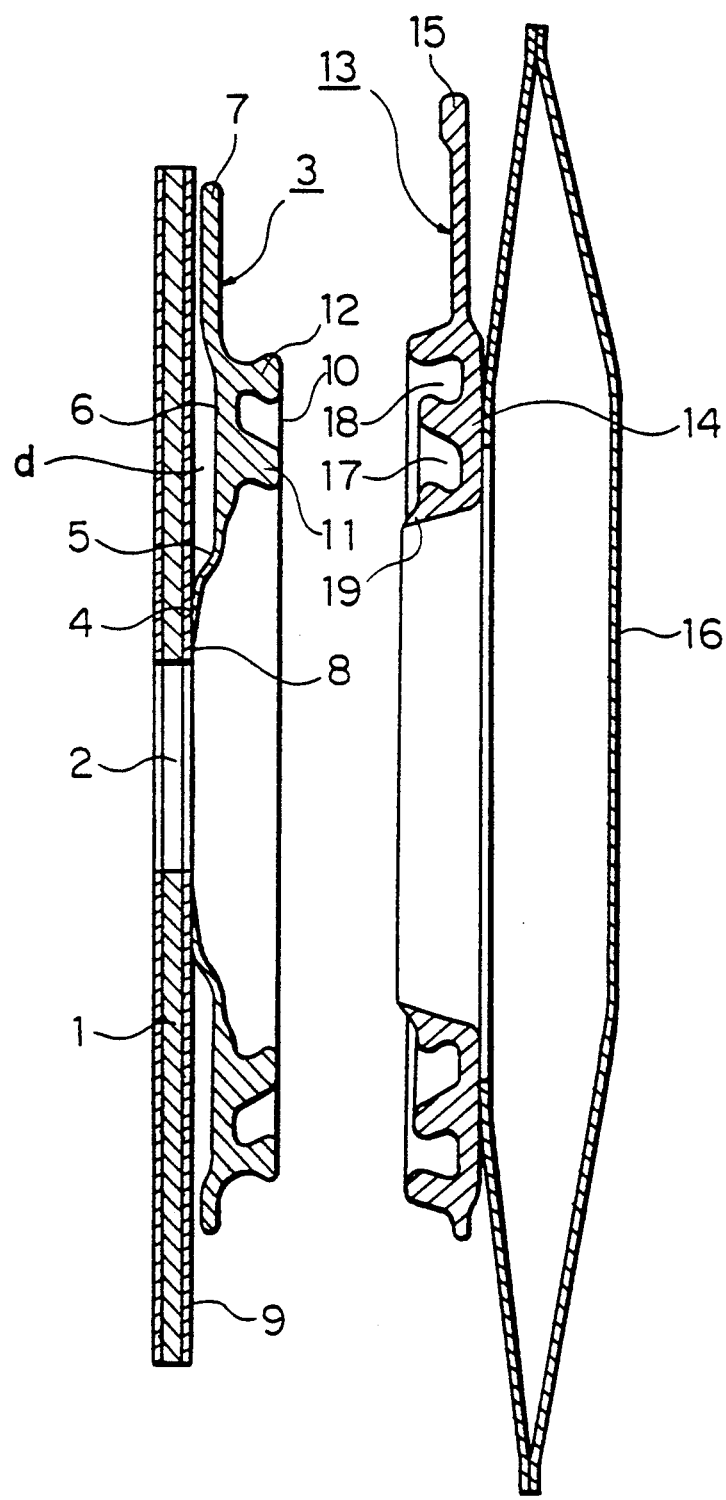
FIG. 1 is a longitudinal cross-sectional view of one embodiment of the present device.
Figure 2A:
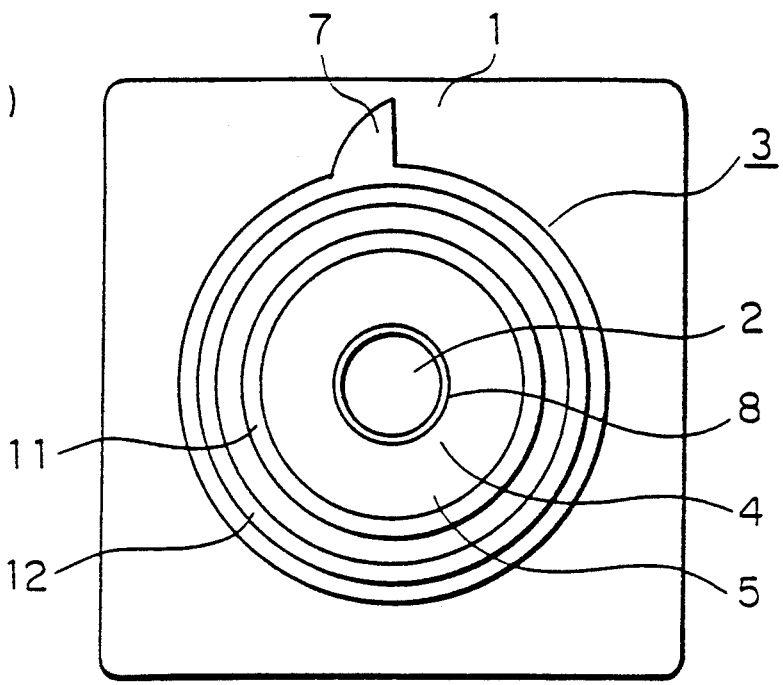
FIGS. 2(a) and 2(b) are front views of each respective member shown in FIG. 1.

Referring to the drawings more particularly by reference numbers wherein like numerals refer to like parts, FIG. 1 illustrates a longitudinal cross-sectional view of one embodiment of the present device wherein the numeral 1 in FIGS. 1 and 2(a) identifies an adhesive plate member having an opening or aperture 2 positioned and located in the center thereof and extending therethrough as shown. The adhesive plate member 1 is shown as being generally square in form, although other shapes can likewise be utilize. A first flange member 3 as best shown in FIG. 1 includes a thin ring-form or annular sealing portion 4, a ring-form or annular taper portion 5 extending outwardly from the annular sealing portion 4, a ring-form or annular fitting portion 6, and a tab portion 7. The sealing portion 4 is concentrically positioned with respect to the opening 2 of the adhesive plate 1 by means of an annular inner periphery 8 which is fixed or otherwise attached, for example, by welding onto the surface of the non-adhesive side surface 9 of the adhesive plate member 1. The sealing portion 4 extends outwardly along the surface 9 of the adhesive plate 1 as shown in FIG. 1. It is also anticipated and recognized that a wide variety of other suitable attachment means may be utilized to fix the sealing portion 4 to adhesive plate surface 9.

Figure 2B:
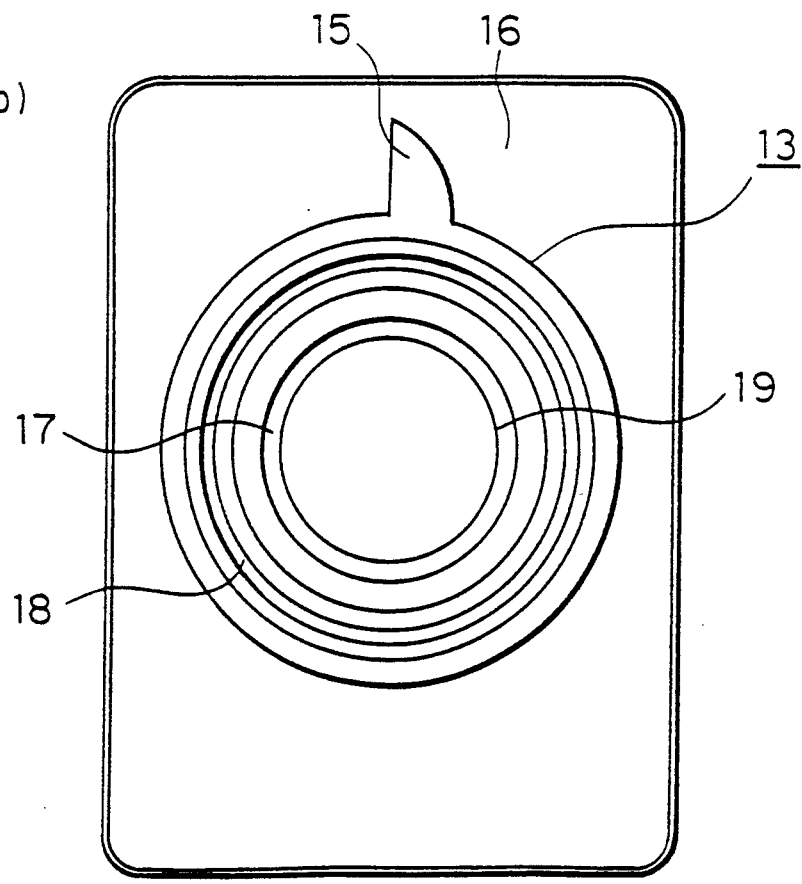

The fitting portion 6 of the first flange member 3 extends outwardly almost in parallel to the adhesive plate 1 beyond a distance from the adhesive plate surface 9 starting from a position somewhat elevated from the level of the sealing portion 4 adjacent the taper portion 5. The annular fitting portion 6 includes a prominence or portion 10 located on the side opposite to the adhesive plate 1 and this prominence 10 includes an inner annular groove formed by projections or chips 11 and 12. A second outer annular flange member 13, separate and apart from the first flange member 3 as best shown in FIGS. 1 and 2(b) includes a ring-form or annular fitting portion 14 and a tab 15 on one side thereof, namely, on the side of the flange 13 facing the adhesive plate 1, and it further includes a bag 16 on the opposite side thereof. Fitting portion 14 includes two annular grooves 17 and 18 which are shaped and dimensioned so as to cooperatively engage the two projections or chips 11 and 12 associated with the portion 10 of the first flange member 3. The fitting portion 14 also further includes a ring-form or annular sealing member or chip 19 which is formed as an extension of the inner side wall associated with the groove 17, the sealing member 19 extending toward or facing the opening 2 associated with the adhesive plate member 1 as best shown in FIG. 1. When the flange members 3 and 13 are cooperatively engaged with each other, the sealing member or chip 19 associated with flange member 13 overlaps under pressure a portion of the fitting portion 6 associated with flange member 3 so as to provide a tight seal therebetween.

Figure 3A:
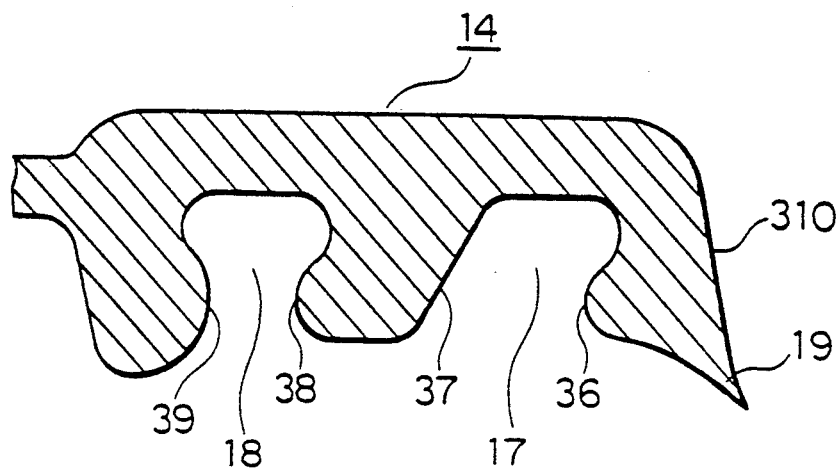
FIGS. 3(a), 3(b) and 3(c) are each enlarged cross-sectional views of the respective fitting portions associated with the first and second members shown in FIG. 1, FIG. 3(c) illustrating the respective fitting portions in their engaged positions.
Figure 3B:
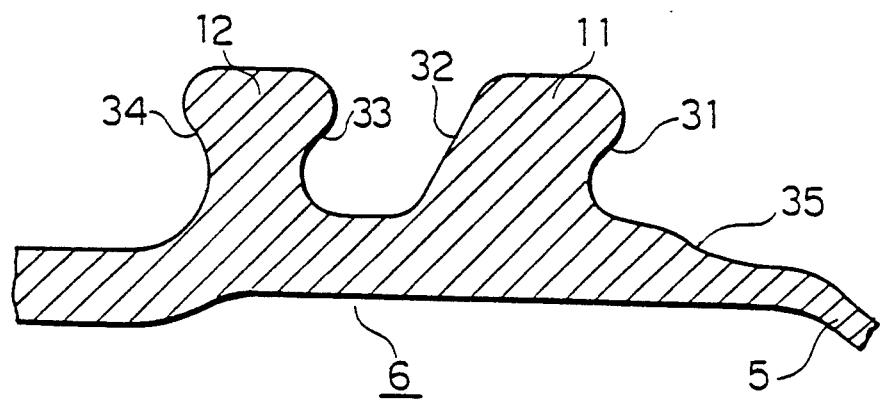
Figure 3C:
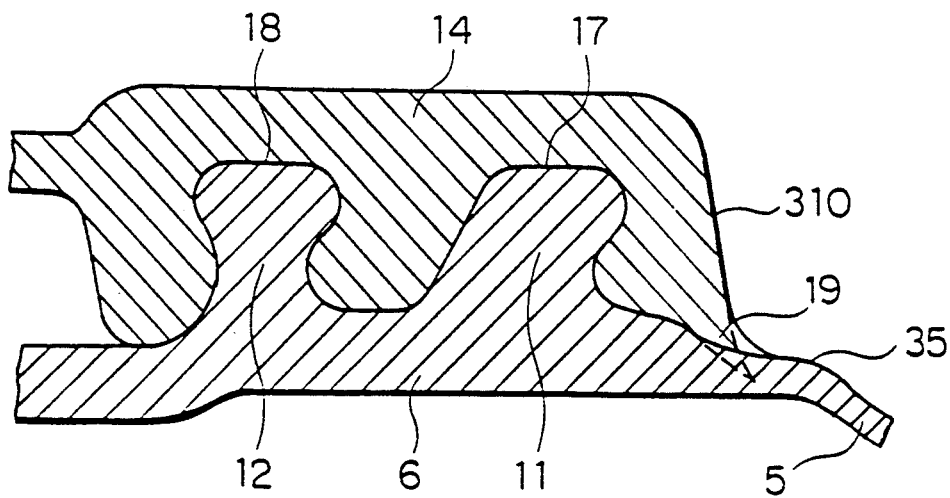

FIGS. 3(a), 3(b) and 3(c) illustrate in detail the construction of the respective fitting portions 6 and 14 associated with the first and second flange members 3 and 13

(FIGS. 3(a) and 3(b)) as well as the cooperative engagement of such fitting portions (FIG. 3(c)). Referring to the inner projection or chip 11 associated with the fitting portion 6 of flange member 3, the inner flank 31 has both concave and convex portions as illustrated in FIG. 3(b). The portion 35 transmitting from the inner projection or chip 11 to the taper portion 5 forms a contacting face for the sealing member or chip 19 associated with the fitting portion 14 of flange member 13 illustrated in FIG. 3(a) and as further described hereinafter. The inner flank 36 of the groove 17 associated with fitting portion 14 likewise has concave and convex portions corresponding to the flank 31 of the first flange 3 and the exterior flank 37 of the inner groove 17 is linear and corresponds to the flank 32 associated with opposite side of the projection or chip 11. Both flanks 38 and 39 associated with the exterior groove 18 of fitting portions 14 have concave and convex portions corresponding to the flanks 33 and 34 associated with the projection or chip 12 of fitting portion 6. Furthermore, the face 310 of the side wall of the inner groove 17 facing the opening 2 extending through adhesive plate 1 slants whereby the sealing member or chip 19 is formed at the terminal end portion thereof as shown in FIGS. 3(a) and 3(c). As evident from FIG. 3(c), flanks 32 and 37 of the inner prominence chip 11 and the inner groove 17 respectively are linear so that both fitting portions 6 and 14 can be guided easily along these linear faces to their proper fitting positions. Furthermore, no excessive force is needed for engaging fitting portions 6 and 14 whereby, under fitted conditions, the sealing chip 19 of the second flange member is pushed up by the contacting face 35 of the first flange member so as to somewhat deform sealing chip 19 thereby causing a biasing force to work between the sealing chip 19 and the contacting face 35 so as to tightly contact them together to form a fluid-tight seal. Therefore, it is important to note that the engagement or fitting between the inner projection or chip 11 and the groove 17 mainly supports the sealing action of sealing member or chip 19, whereas the engagement or fitting between the projection or chip 12 and the groove 18 mainly supports the locking action. The overall thickness of the fitting portion 6 and 14 can be controlled and made thinner by taking partial charge of the sealing action and locking action in this way. The dotted outline form shown in FIG. 3(c) illustrates the original shape of the sealing chip 19 in the non-fitted or unengaged state, and it is appreciated that the shape of chip 19 deforms from this position to the engaged position shown in solid outline form.

As for the materials used in the contruction of adhesive plate 1, this member is made from a sheet form material consisting of a hydrophillic water-absorbing polymer and a hydrophobic viscous polymer, each product obtained by coating adhesive on a foaming sheet or film or product having viscous reinforcing tape on the outer periphery, and having on the surface a film such a polyethylene, chlorinated polyethylene, ethylene-vinyl acetate copolymer, ethylene-ethyl acrylate copolymer, ethylene-methyl acrylate copolymer, polypropylene, polyvinyl chloride, polyester, polyamid or the like, or films obtained by laminating appropriately the above-identified films may likewise be used.

Figure 4:
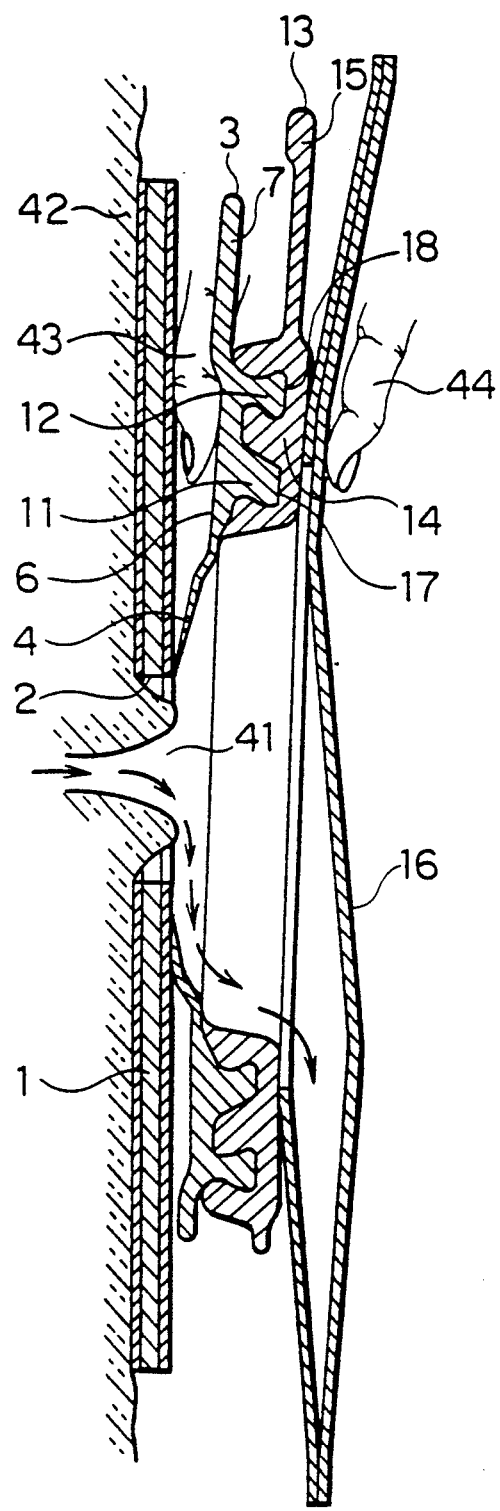
FIG. 4 is an explanatory drawing illustrating how to attach the device of FIG. 1 to a patient.

As for the material used in the construction of the first flange member 3, an ethylene-ethyl acrylate copolymer is most preferred; an ethylene-methyl acrylate copolymer, ethylene-vinyl acetate copolymer, ethylene-methyl methacrylate copolymer is more preferred; and polyethylene, vinyl chloride, ethylene-acrylic acid copolymer, ethylene-methacrylic acid copolymer, polyethylene chloride, thermoplastic elastomer or the like may be used. Appropriate thickness of the thin sealing portion 4 of the first flange 3 is not more than 1 mm, preferably not more than 0.5 mm, and the appropriate width thereof is in the range of about 1 to 10 mm, preferably about 4 to 6 mm. If the width of sealing portion 4 is less than 4 mm, it is difficult to insert a finger underneath the flange 3 as shown in FIG. 4 as will be hereinafter further described. The scope of width exceeding 6 mm should be avoided because such a big diameter of opening cannot be taken. For adhereing the first flange 3 to the adhesive plate 2, a variety of means may be utilized such as a method of welding under heating from the first flange, a method of welding a film forming part of the adhesive plate to the first flange with a high frequency welder or supersonic welder and sticking the film on the faceplate, a method of using adhesives, and the like. Other known suitable means for accomplishing this task may also be used.

The same material used in the construction of the first flange 3 may also be used for construction of the second flange 13. The bag 16 may be welded to the second flange by means of thermal welding, high frequency welding, supersonic welding, adhesion with adhesives or the like. Furthermore, a cap-type flange, stopper or the like may be set or used in place of the pouch 16.

Operation and use of the present ostomy appliance will now be explained with reference to FIG. 4. The adhesive plate 1 is adhered onto a person's skin 42 so that the opening 2 may superimpose on and be in registration with the aperture of a living body, for example, stoma 41. Then, the finger 43 is allowed to slide below the fitting portion 6 while the first flange 3 is somewhat raised with such finger. In this case, there is no difficulty in inserting the finger 43 because the sealing portion 4 being relatively thin has flexibility and a slight distance d occurs between the fitting portion 6 and the adhesive plate 1 as shown in FIG. 1. Both flanges 3 and 13 are coupled together as a whole along the entire ring or annular periphery of such members by superimposing the second flange 13 onto the first flange 3 and pressing both flanges together with the finger 44 positioned to the exterior side of the second flange 13 and the finger 43 inserted below the first flange 3 as shown in FIG. 4. This pressing action enables the prominence projections 11 and 12 of the fitting portion 6 to be fitted into and engaged with the grooves 17 and 18 of the fitting portion 14. As already explained with reference to FIG. 3, in this case, both prominences or projections 11 and 12 of the fitting portion 6 are fitted into the corresponding grooves 17 and 18 of the fitting portion 14 and, at the same time, the sealing chip 19 at the terminal end of the inner most flank 310 deforms somewhat to oppressively adhere onto the contacting face 35 of the fitting portion 6. This forms a slanting face outwardly extending from the opening 2 of the adhesive plate 1 to the sealing portion 4, the taper portion 5, the surface of the sealing chip 19 and the face 310. The waste products discharged from the stoma 41 will flow along the slanting face described above as shown by the arrow marks in FIG. 4 and such waste products will then be collected in the bag 16. In this case, the waste products smoothly flow toward the bag without invading between both flanges and without lodging or otherwise remaining in the openings of both flanges.

When the bag 16 is washed or replaced by a new bag or a cap-type flange, the second flange 13 is easily removed from the first flange by forcing in the opposite direction to peel the second flange 13 away from the first flange 3 while holding both tabs 7 and 15.

In the embodiment of the present invention illustrated in FIGS. 1–4 and described above, the fitting portion 6 of the first flange 3 was made prominent, that is, it includes the projections or chips 11 and 12, whereas the fitting portion 14 of the second flange 13 was grooved to included corresponding grooves 17 and 18. It is important to recognize that the construction of the fitting portions 6 and 14 may be reversed such that the fitting portion 6 of the first flange 3 may be grooved and the fitting portion 14 of the second flange 13 may be prominent. Furthermore, it is also recognized that the sealing chip 19 may be formed in the prominent fitting portion instead of the grooved fitting portion.

Figure 5:
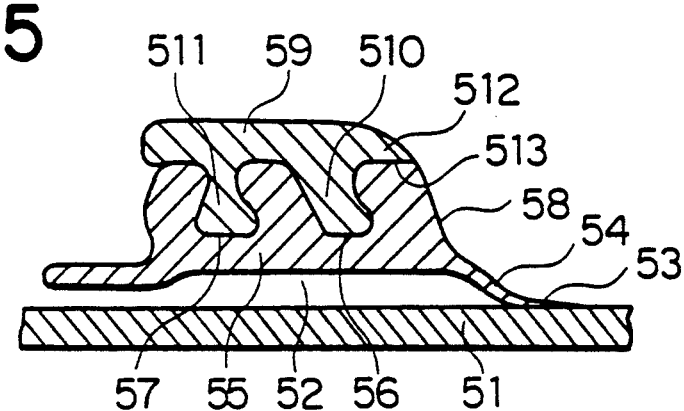
FIGS. 5 to 8 are respective partial cross-sectional views illustrating other embodiments of fitting portions of the present device.

FIGS. 5-8 illustrate other emobidments of the present appliance as hereinafter explained. In FIG. 5, the member 51 represents the adhesive plate member and the member 52 represents the first flange member which includes an annular sealing portion 53, an annular taper portion 54, and an annular fitting portion 55. The fitting portion 55 has two annular grooves 56 and 57. Only one flank of inner groove 56 in the opening side is linear, the other flanks all being formed in appropriate concave and convex portions with the inner most flank 58 which faces the opening 2 slanting as shown so as to follow the taper portion 54. Annular fitting portion 59 is associated with the second flange and has two annular prominence chips or projections 510 and 511, the sealing member or chip 512 being located adjacent the inner most portion thereof facing the opening 2 as shown. When chips or projections 510 and 511 are fitted into and cooperative engage the corresponding grooves 56 and 57, the sealing member or chip 512 oppressively contacts the contacting face 513 of the first flange by deforming somewhat whereby the surfaces from the sealing portion 53, the taper portion 54, the inner most flank 58, and the sealing chip 512 form a series of outwardly extending slanting faces for the purpose of allowing discharged waste products to easily flow therealong as previously described.

Figure 6:
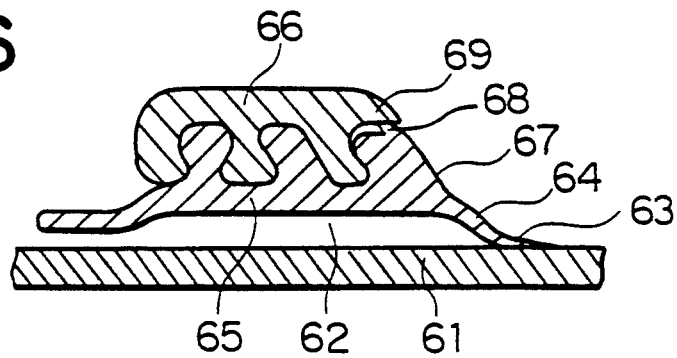

FIG. 6 illustrates another embodiment wherein the member 61 represents the adhesive plate and the member 62 represents the first flange which includes an annular fitting portion 63, an annular taper portion 64, and an annular fitting portion 65. The reference numeral 66 represents the annular fitting portion of the second flange. The fitting portions 65 and 66 include three annular prominent chips or projections and two annular grooves respectively. Only one opposing face or flank is linear, all other opposing faces or flanks having appropriate concave and convex portions as shown. The inner most face 67 of fitting portion 65 in the first flange facing the opening 2 is slanted as shown, and at the top portion thereof is located the tapered annular sealing chip 68. As with the other sealing members, the sealing chip 68 deforms in the fitted state and oppressively contacts the inner most portion 69 of the fitting portion 65 in the second flange facing the opening 2. In this case, also, the sealing portion 63, the taper portion 64, and the inner most flank 67 of the fitting portion 65 in the first flange, as well as the outer surface of the sealing chip 68 and the outer surface of the inner most portion 69 of the second flange form a series of outwardly extending slanting faces for the same purpose as previously indicated.

In all the embodiments above, plural prominent chips or projections and plural grooves are shown in both flanges, whereby one engaged combination accomplishes mainly a sealing action and the other engaged combination accomplishes mainly a locking action. It is also recognized and anticipated that the sealing and locking action achieved by the construction of the respective fitting portions can be attained through the use of one prominent chip and one groove. Such embodiments will now be discussed.

Figure 7:
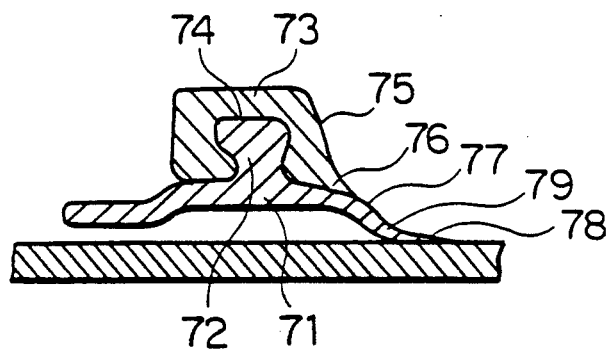

FIG. 7, illustrates another embodiment of the present device wherein the annular fitting portion of the first flange member is fixed or otherwise attached to the adhesive plate member as previously described and such portion 71 includes one prominent chip or projection 72. The annular fitting portion 73 of the second flange similarly includes only one annular groove 74. Again, the inner most face 75 facing the opening 2 is slanted and equipped with the annular sealing chip 76 at its terminal end as shown. In the fitted state, the sealing chip 76 likewise deforms and oppressively contacts the contacting face 77 of the fitting portion 71 in the first flange. The sealing portion 78 and the taper portion 79 associated with the first flange member and the inner most face 75 of the fitting portion 73 in the second flange form a series of slanting faces for the reasons previously discussed.

Figure 8:
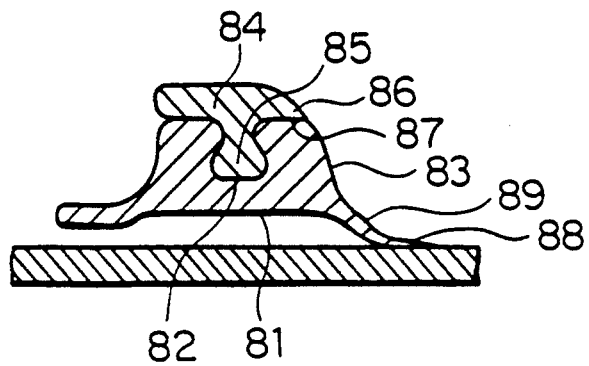

FIG. 8 illustrates still another embodiment of the present appliance wherein the annular fitting portion 81 of the first flange member is again fixed to the adhesive plate member by means previously described and such portion 81 includes one groove 82 and an inner most face 83 which is slanted so as to again face the opening 2. The annular fitting portion 84 of the second flange similarly includes a single cooperatively engageable chip or projection 85 as well as the annular sealing chip 86 which is located at the tip of the inner most portion thereof facing the opening 2 as shown. In the fitted state, the sealing chip 86 again deforms and oppressively contacts the contacting face 87 of the fitting portion 81 in the first flange, and a series of slanting faces is likewise formed by and between the sealing portion 88, the taper portion 89, and the inner most face 83 of the first flange member and the outer surface of the sealing chip 86.

In the embodiments of FIGS. 7 and 8, both the sealing action and the locking action is accomplished by a single cooperatively engaged projection and groove associated with the respective fitting portions of the two flange members. As a result, in comparison with the embodiments in FIGS. 1-6, the embodiments illustrated in FIGS. 7 and 8 appear to be somewhat inferior and less reliable, although such constructions likewise fulfill all of the objects and advantages of the present invention and there are no practical problems associated with their use and operation.

According to the present device, the following advantages and effects can be attained.

(1) Effective diameter of the opening in the adhesive plate can be enlarged.

Since the first flange member is equipped with an annular sealing portion and the annular fitting portion is located close to this annular sealing portion, when the inner periphery of the annular sealing portion is directly adhered to the non-adhesive side of the adhesive plate, the annular sealing portion is positioned very close to the annular fitting portion. Thus, the opening through the adhesive plate can be enlarged without enlarging particulary the outer diameter of the adhesive plate.

(2) Thickness can be thinned.

The shape of the fitting portion can be defined in view of the fitting function only, since the fitting portion and the sealing chip each have an independent structure. There is no need of height in the fitting portion to achieve the sealing action as heretofore needed in prior art constructions since the concave and convex shape of the projections and grooves enables such engagement to achieve a tighter fit therebetween without increasing height. As the result, the size of the fitting portion can be made smaller and its thickness can be thinned to about 40% of the known appliances.

(3) Sealing function enables waste matter to flow smoothly into the device.

The inner most portion of the fitting portion facing the opening of the adhesive plate is equipped with a sealing chip which is of a structure different from the fitting structure, and as both fitting portions of the present device are fitted together, the sealing chip is devised to exert an oppressive force or biasing action on the opposed fitting portion. As far as the fitting is carried out, the accurate sealing function can be kept, and waste products can flow smoothly along the outer face of the sealing chip without invasion between both flanges.

(4) It's operation is easy.

Since the first flange member can be easily lifted from the adhesive plate because of the flexibility of the thin annular sealing portion and the gap formed between the fitting portion and the adhesive plate, the second flange member can be easily engaged to and disengaged from the first flange member by inserting a finger along the back side of the first flange member. This construction facilitates the smooth flow of waste products to the bag or other collecting means without allowing such waste to leak into or collect in the coupling portion of both flanges. Therefore, the installation and removal of the second flange member during use can be effected sanitarily without being bothered with waste product stains and the like.

(5) Wearing of the appliance is favorable.

Since, as described above, thickness and size of the flange members can be reduced and the first flange member has been constructed so as to be in a somewhat suspended state from the adhesive plate by the annular sealing portion, there is very little feeling or sense of incompatibility to the skin during use. Also, the wearing of the present appliance does not attract people's attention when thin summer clothes are worn. Furthermore, there is no need of feeling anxiety at all because proper and secure fitting and sealing of the present device will preclude any danger of leakage.

Thus, there has been shown and described several embodiments of a novel two-piece ostomy appliance, which constructions fulfill all of the objects and advantages sought therefor. Many changes, modifications, variations, and other uses and applications of the present constructions will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. An ostomy appliance for attachment around an aperture of a human body, said ostomy appliance comprising a plate member having an opening extending therethrough, one side of said plate member being an adhesive side having adhesive means associated therewith for adhesively attaching said plate member around the aperture of the human body such that the opening through said plate member is placed in registration with said body aperture, said plate member having a non-adhesive side located opposite said adhesive side, a first flange member located adjacent the non-adhesive side of said plate member, said first flange member including an annular sealing portion extending around the opening through said plate member and an annular coupling portion located radially outwardly of said annular sealing portion, said annular sealing portion having a radially innermost inner periphery located adjacent to the opening through said plate member, said inner periphery being attached to said plate member around said opening extending therethrough, a second flange member having a passageway extending therethrough and including an annular coupling portion extending around said passageway on one side portion thereof, the coupling portions of said first and second flange members having cooperatively engageable means thereon for securely coupling said flange members together along said coupling portions, said second flange member further including collecting means associated with the opposite side thereof, said collecting means being positioned and located such that the passageway through said second flange member serves as inlet means for said collecting means, said passageway through said second flange member lying in communication with the opening through said plate member when said first and second flange members are cooperatively engaged with each other, said appliance further including annular sealing means positioned and located on one of the flange members radially inwardly of the annular coupling portion thereof such that when said first and second flange members are coupled together said sealing means exerts a biasing force against a contacting face on the other of said flange members forming an annular seal therebetween, said annular sealing means including a slanting face facing towards the opening through said plate member, said slanting face tightly abutting said contacting face to form a substantially continuous inner surface.

2. The ostomy appliance defined in claim 1 wherein a space is formed between said first flange member and the non-adhesive side of said plate member, said space being defined from a point somewhat adjacent to the outer periphery of said annular sealing portion to the outer edge portions of said first flange member.

3. The ostomy appliance defined in claim 1 wherein said first flange member further includes an annular tapered portion, said annular tapered portion being positioned and located so as to connect the radially outermost portion of said annular sealing portion with the inner periphery of said annular coupling portion.

4. The ostomy appliance defined in claim 1 wherein the cooperatively engageable means associated with the coupling portions of said first and second flange members includes a plurality of correspondingly spaced annular projections and annular grooves, said plurality of spaced annular projections being associated with one of said coupling portions and said plurality of said spaced annular grooves being associated with the other of said coupling portions.

5. The ostomy appliance defined in claim 1 wherein the cooperatively engageable means associated with the coupling portions of said first and second flange members includes a projection associated with one of said coupling portions and a groove associated with the other of said coupling portions, said projection being cooperatively engageable with said groove when said coupling portions are engaged with each other.

6. The ostomy appliance defined in claim 1 wherein said sealing means is associated with the annular coupling portion of said first flange member.

7. The ostomy appliance defined in claim 1 wherein said sealing means is associated with the annular coupling portion of said second flange member.

8. The ostomy appliance defined in claim 1 wherein said sealing means includes resilient means located adjacent the radially inner most portion of the coupling portion of said first flange member on the side thereof facing the opening in said plate member, said resilient means exerting a biasing force against the coupling portion of said second flange member so as to form a pressure tight seal therebetween at such point of joinder.

9. The ostomy appliance defined in claim 1 wherein said sealing means includes resilient means located adjacent the radially inner most portion of the coupling portion of said second flange member on the side thereof facing the opening in said plate member, said resilient means exerting a biasing force against the coupling portion of said first flange member so as to form a pressure tight seal therebetween at such point of joinder.

10. The ostomy appliance defined in claim 1 wherein said collecting means includes a bag member.

11. The ostomy appliance defined in claim 10 wherein said bag member is removably attachable to said second flange member.

12. The ostomy appliance defined in claim 1 wherein said first and second flange members each include a tab member, each of said tab members being positioned and located so as to facilitate grasping by a person.

13. Ostomy appliance for affixing to a human body around an aperture thereof, said ostomy appliance comprising an adhesive plate having opposite sides including a side fixable by adhesion to a human body and a non-adhesive side, said adhesive plate having an opening therethrough corresponding to an aperture of a human body, a first flange located adjacent the non-adhesive side of said adhesive plate, said first flange including a thin ring form sealing portion extending around the opening through said adhesive plate, said ring form sealing portion having a radially innermost inner periphery secured to said adhesive plate around said opening therethrough, said first flange including a first ring form fitting portion located radially outwardly of the ring form sealing portion, a second flange capable of fitting to said first flange, said second flange having a second ring form fitting portion on one side thereof and a pouch or cap on an opposite side thereof, said second ring form fitting portion being capable of fitting to said first ring form fitting portion, at least one ring form prominence on one of said ring form fitting portions cooperatively engageable with a like number of ring form grooves on the other of said ring form fitting portions, a ring form sealing chip located on one of said first and second flanges radially inwardly of the ring form fitting portion thereof, said ring form sealing chip exerting a biasing force against the other of said first and second flanges radially inwardly of the ring form fitting portion thereof when said first and second flanges are fitted together forming a ring form seal therebetween, and said ring form sealing chip having a radially inwardly facing slanting face which tightly mates with the other of said flanges to form a substantially continuous radially inwardly facing surface.

* * * * *